United States Patent
Walsh

(10) Patent No.: US 7,425,411 B2
(45) Date of Patent: Sep. 16, 2008

(54) METHOD FOR RECOVERING MICROORGANISMS FROM A SAMPLE

(75) Inventor: John D. Walsh, Durham, NC (US)

(73) Assignee: bioMerieux, Inc., Durham, NC (US)

( * ) Notice: Subject to any disclaimer, the term of this patent is extended or adjusted under 35 U.S.C. 154(b) by 250 days.

(21) Appl. No.: 11/008,398

(22) Filed: Dec. 9, 2004

(65) Prior Publication Data

US 2005/0124027 A1   Jun. 9, 2005

Related U.S. Application Data

(60) Provisional application No. 60/527,927, filed on Dec. 9, 2003.

(51) Int. Cl.
*C12N 1/02* (2006.01)
*C12N 1/20* (2006.01)
*C12Q 1/00* (2006.01)
*C12Q 1/22* (2006.01)

(52) U.S. Cl. .................. 435/4; 435/261; 435/252.3; 435/29; 435/31; 435/32; 435/34

(58) Field of Classification Search ............ None
See application file for complete search history.

(56) References Cited

U.S. PATENT DOCUMENTS

| | | | |
|---|---|---|---|
| 4,632,902 A | 12/1986 | Waters et al. | |
| 5,496,706 A | 3/1996 | Kuusela et al. | |
| 5,989,821 A | 11/1999 | Goh et al. | |
| 6,156,507 A | 12/2000 | Hiramatsu et al. | |
| 6,312,903 B1 | 11/2001 | Jannes et al. | |
| 2002/0055101 A1 | 5/2002 | Bergeron et al. | |
| 2002/0086289 A1 | 7/2002 | Straus | |
| 2002/0147317 A1 | 10/2002 | Bentsen et al. | |
| 2002/0160503 A1 * | 10/2002 | Maresch et al. | 435/252.3 |
| 2003/0054436 A1 | 3/2003 | Kunsch et al. | |
| 2003/0100104 A1 | 5/2003 | Jeffrey et al. | |

FOREIGN PATENT DOCUMENTS

| | | |
|---|---|---|
| EP | 0597542 | 5/1994 |
| WO | WO 98/32874 | 7/1998 |
| WO | WO02/064086 | 8/2002 |
| WO | WO 02/079486 | 10/2002 |
| WO | WO 02/082086 | 10/2002 |

OTHER PUBLICATIONS

Hirsch, JG et al (1960) Studies of phagocytosis of group A streptococci by polymorphonuclear leucocytes in vitro. J Exp Med, 1960, vol. 111, pp. 309-322.*
Garcia A et al (1996) Comparison of two leukocyte extraction methods for cytomegalovirus antigenemia assay. J Clin Microbiol, vol. 34, No. 1, pp. 182-184.*
Herzberg MC et al (Mar. 1983) Aggregation of human platelets and adhesion of *Streptococcus sanguis*. Infection and Immunity, vol. 39, No. 3, pp. 1457-1469.*
Written Opinion of the International Searching Authority from related PCT/US04/41498 completed Jul. 28, 2005.*

* cited by examiner

*Primary Examiner*—Lisa J Hobbs
(74) *Attorney, Agent, or Firm*—Myers Bigel Sibley & Sajovec, P.A.

(57) ABSTRACT

The present invention provides for a method for recovering microorganisms from a sample that is rapid and provides microorganisms substantially free of adsorbents and other particles. The method includes mixing a sample comprising a medium, an adsorbent and microorganisms with a first solution in a first vessel; separating the adsorbent from the medium and the microorganisms and removing the microorganisms and a portion of the medium from the first vessel; mixing the microorganisms and the portion of the medium with a second solution in a second vessel to resuspend the microorganisms; and separating the microorganisms from the resulting mixture.

18 Claims, No Drawings

METHOD FOR RECOVERING MICROORGANISMS FROM A SAMPLE

CROSS-REFERENCE TO RELATED APPLICATIONS

This application claims the benefit of U.S. Provisional Patent Application No. 60/527,927 filed on Dec. 9, 2003.

FIELD OF THE INVENTION

The present invention relates to a method for recovering microorganisms from a sample. More particularly, the present invention relates to a method for recovering microorganisms from a sample wherein the microorganisms are substantially free from adsorbents and other particles.

BACKGROUND OF THE INVENTION

The direct analysis of positive blood culture broth using rapid ID/AST systems such as VITEK (bioMerieux, Inc.) has become more widespread as several studies have confirmed the significant benefits of a rapid result. Direct testing from BacT/ALERT FAN bottles (FA, FN or PF) (bioMerieux, Inc.) is complicated by the presence of charcoal particles which make it difficult to prepare a suitable microbial suspension. In particular, the separation of microorganisms from the activated charcoal present in BacT/ALERT FAN bottles has proven to be very difficult due to the broad particle size distribution of the charcoal and the presence of very fine particles not much larger than many microorganisms.

Previous attempts at recovering microorganisms free from adsorbents such as charcoal particles included the use of a polymeric flocculent that agglutinated charcoal particles and resulted in rapid sedimentation. This reagent was however mildly toxic to *S. aureus* upon prolonged exposure. Furthermore, its optimal concentration was affected by the type of microorganism and whether hemolysis was present in the sample.

Thus, there is a need in the art for a rapid, accurate and inexpensive means for recovering microorganisms from samples wherein the microorganisms are free from particles including adsorbents.

SUMMARY OF THE INVENTION

The present invention provides for a method for recovering microorganisms from a sample which is rapid and provides microorganisms substantially free of adsorbents and other particles. The method comprises the steps of:
  (a) mixing a sample comprising a medium, an adsorbent and microorganisms with a first solution in a first vessel;
  (b) separating the adsorbent from the medium and the microorganisms and removing the microorganisms and a portion of the medium from the first vessel;
  (c) mixing the microorganisms and the portion of the medium with a second solution in a second vessel to resuspend the microorganisms; and
  (d) separating the microorganisms from the resulting mixture of step (c).

The present invention also provides for another method for recovering microorganisms from a sample. This method comprises the steps of:
  (a) preparing a sample comprising a medium, an adsorbent and microorganisms;
  (b) mixing the sample with a first solution in a first vessel;
  (c) separating the adsorbent from the medium and the microorganisms and removing the microorganisms and a portion of the medium from the first vessel;
  (d) mixing the microorganisms and the portion of the medium with a second solution in a second vessel to resuspend the microorganisms; and
  (e) separating the microorganisms from the resulting mixture of step (d).

The present invention also provides for another method for recovering microorganisms from a sample. This method comprises the steps of:
  (a) preparing a sample comprising a medium, an adsorbent, microorganisms and blood or a blood component;
  (b) mixing the sample with a first solution in a first vessel, the first solution comprising dextran and calcium chloride;
  (c) separating the adsorbent and the blood or blood component from the medium and the microorganisms and removing the microorganisms and a portion of the medium from the first vessel;
  (d) mixing the microorganisms and the portion of the medium with a second solution in a second vessel to resuspend the microorganisms; and
  (e) separating the microorganisms from the resulting mixture of step (d).

The above-described methods are applicable across a broad range of microorganisms and the first solution is not very toxic. Microorganisms that can be separated from particles using these methods include, but are not limited to, *Staphylococcus aureus, Staphylococcus epidermidis, E. coli, E. faecalis, N. meningitidis, S. pyogenes, P. aeruginosa, Stenotrophomonas maltophilia, Micrococcus luteus, Streptococcus pneumoniae* and *Candida albicans*.

DETAILED DESCRIPTION OF THE INVENTION

As stated above, the present invention provides for a method for recovering microorganisms from a sample which is rapid and provides microorganisms substantially free of adsorbents and other particles. The method comprises the steps of:
  (a) mixing a sample comprising a medium, an adsorbent and microorganisms with a first solution in a first vessel;
  (b) separating the adsorbent from the medium and the microorganisms and removing the microorganisms and a portion of the medium from the first vessel;
  (c) mixing the microorganisms and the portion of the medium with a second solution in a second vessel to resuspend the microorganisms; and
  (d) separating the microorganisms from the resulting mixture of step (c).

Microorganisms that can be separated from particles using this method and any of the methods of the present invention include, but are not limited to, *Staphylococcus aureus, Staphylococcus epidermidis, E. coli, E. faecalis, N. meningitidis, S. pyogenes, P. aeruginosa, Stenotrophomonas maltophilia, Micrococcus luteus, Streptococcus pneumoniae* and *Candida albicans*.

Samples that can be used in this method of the present invention can be obtained from any source including, but not limited to, blood, blood products, tissue, ascites, culture media, body fluids, skin, pus, uro-genital specimens, feces, foodstuffs, beverages, cosmetic products, pharmaceutical products, healthcare products, surfaces such as floors and tables, and airborne particles such as pollen and dust. The sample may be one that is suspected of having microorganisms or the sample may already have been tested for the presence of microorganisms and have tested positive for microorganisms. The sample will require the addition of a medium prior to step (a) if it does not include any medium and the medium is preferably a growth medium. The sample will require the addition of an adsorbent prior to step (a) if it does not include any adsorbent. The amount of medium and/or adsorbent to add to the sample will be dependent upon the estimated number of microorganisms in the sample and could easily be ascertained by one skilled in the art. It is suggested, though, that the amount of adsorbent in the sample range from about 1-5% weight/volume of the sample.

Adsorbents that can be used generally comprise of at least one of the following: aluminum oxide, colloidal native hydrated aluminum silicates, crystalline hydrated alkali-aluminum silicates, silica, siliceous frustules, fragments of various species of diatoms, amorphous carbon, ion exchange resins, non-functional polymeric resin adsorbents, polystyrene resin cross-linked with divinyl benzene, charcoal particles, activated charcoal, charcoal bound to fibers, fuller's earth bound to fibers, charcoal bound to fuller's earth and combinations thereof. Preferably, the adsorbent comprises activated charcoal.

Step (a) provides that the sample and first solution are mixed in a vessel and this can be accomplished by briefly vortexing the vessel. The vessel is preferably a conical tube.

The amount of first solution and sample mixed in step (a) should in a ratio of about 1 mL of first solution per about 4 mL of sample. Preferably, the amount of sample is 8 mL and the amount of first solution mixed with sample is 2 mL.

The first solution preferably comprises a polysaccharide. Further, the polysaccharide is preferably dextran. Preferably, dextran used with this method has a molecular weight of about 40 to 210 kD and more preferably a molecular weight of about 70 kD. Also, the amount of dextran in the first solution is about 20 to 40% weight/volume of the first solution and most preferably about 30% weight/volume of the first solution. Dextran can be obtained from several companies including Pharmacia. It is further preferable that the first solution comprises a salt solution. The amount of salt solution in the first solution is preferably about 0.5 M to 1.5 M and more preferably about 0.7 M. Salt solutions that can be used with the present invention include, but are not limited to, sodium chloride, calcium chloride, potassium chloride, magnesium chloride, magnesium sulfate, ammonium chloride and lithium chloride. Preferably, the salt solution comprises calcium chloride. It has been found that the salt solution exerts an aggregating effect on the adsorbent.

The above method provides for separating the adsorbent from the microorganisms and the medium and removing the microorganisms and a portion of the medium from the vessel. Preferably, the adsorbent can be separated from the microorganisms and medium by centrifugation or filtration. Most preferably, the adsorbent is separated from the microorganisms and medium by centrifugation for ten (10) minutes at $\geqq 1,000$ G to pellet the adsorbent and other particles such as red blood cells.

Step (c) of the above method provides for mixing the microorganisms and a portion of the medium with a second solution in a second vessel to resuspend the microorganisms. After the second solution is added to the vessel, the vessel can be vortexed.

The amount of the second solution that can be added to the vessel in step (c) is dependent upon the milliliters of microorganisms and medium mixed into the second vessel. Generally, about 2 mL of the second solution should be added for every 1 mL of the microorganisms and medium mixed into the second vessel. In a preferred embodiment, 5 mL of microorganisms and medium is mixed into the second vessel with 10 mL of the second solution. Preferably, the second solution comprises a buffered salt solution and/or a saline solution. A preferred saline solution is 0.45% NaCl.

The above method provides for separating the microorganisms from the resulting mixture of step (c). Preferably, this can be done by centrifugation or filtration. Most preferably, this can be done by centrifugation for fifteen (15) minutes at $\geqq 3,000$ G to pellet the microorganisms.

Also, the microorganisms obtained in step (d) can be resuspended in a buffered salt solution or saline solution again if desired.

Preferably, the sample in step (a) further comprises plasma, serum, cells, blood or a blood component. Samples can be obtained from a source such as blood, blood products, tissue, body fluids, skin, pus, etc., that already include plasma, serum, cells, blood or a blood component. If the sample does not include plasma, serum, cells, blood or a blood component, any of these may be added to the sample prior to step (a). If plasma or serum is included in the sample, the bulk of the plasma or serum is separated along with the medium and the microorganisms from the adsorbent in step (b) and then from the microorganisms in step (d). If blood or a blood component is included in the sample, the blood or blood component is separated along with the adsorbent from the medium and microorganisms in step (b).

The present invention also provides for another method for recovering microorganisms from a sample. This method comprises the steps of:

(a) preparing a sample comprising a medium, an adsorbent and microorganisms;
(b) mixing the sample with a first solution in a first vessel;
(c) separating the adsorbent from the medium and the microorganisms and removing the microorganisms and a portion of the medium from the first vessel;
(d) mixing the microorganisms and the portion of the medium with a second solution in a second vessel to resuspend the microorganisms; and
(e) separating the microorganisms from the resulting mixture of step (d).

Step (a) provides for preparing a sample comprising a medium, an adsorbent and microorganisms. The type of sample to be tested will determine how the sample will be prepared. Samples that can be used in this method of the present invention can be obtained from any source including, but not limited to, blood, blood products, tissue, ascites, culture media, body fluids, skin, pus, uro-genital specimens, feces, foodstuffs, beverages, cosmetic products, pharmaceutical products, healthcare products, surfaces such as floors and tables, and airborne particles such as pollen and dust. The sample may be one that is suspected of having microorganisms or the sample may already have been tested for the presence of microorganisms and have tested positive for microorganisms. The sample may require the addition of a medium and/or the sample may require the addition of an adsorbent. The amount of medium and/or adsorbent to add to the sample will be dependent upon the estimated number of microorganisms in the sample and could easily be ascertained by one skilled in the art. It is suggested, though, that the amount of adsorbent in the sample range from about 1-5% weight/volume of the sample.

Preferably, the sample in step (a) further comprises plasma, serum, cells, blood or a blood component. Samples can be obtained from a source such as blood, blood products, tissue, body fluids, skin, pus, etc., that already include plasma, serum, cells, blood or a blood component. If the sample does not include plasma, serum, cells, blood or a blood component, any of these may be added to the sample during step (a). If plasma or serum is included in the sample, the bulk of the plasma or serum is separated along with the medium and the microorganisms from the adsorbent in step (c) and then from the microorganisms in step (e). If blood or a blood component is included in the sample, the blood or blood component is separated along with the adsorbent from the medium and microorganisms in step (c).

Adsorbents that can be used with this method generally comprise of at least one of the following: aluminum oxide, colloidal native hydrated aluminum silicates, crystalline hydrated alkali-aluminum silicates, silica, siliceous frustules, fragments of various species of diatoms, amorphous carbon, ion exchange resins, non-functional polymeric resin adsorbents, polystyrene resin cross-linked with divinyl benzene, charcoal particles, activated charcoal, charcoal bound to fibers, fuller's earth bound to fibers, charcoal bound to fuller's earth and combinations thereof. Preferably, the adsorbent comprises activated charcoal.

Step (b) provides that the sample and first solution are mixed in a vessel and this can be accomplished by briefly vortexing the vessel. The vessel is preferably a conical tube.

The amount of first solution and sample mixed in step (b) should in a ratio of about 1 mL of first solution per about 4 mL of sample. Preferably, the amount of sample is 8 mL and the amount of first solution mixed with sample is 2 mL.

The first solution preferably comprises a polysaccharide. Further, the polysaccharide is preferably dextran. Preferably, dextran used with this method has a molecular weight of about 40 to 210 kD and more preferably a molecular weight of about 70 kD. Also, the amount of dextran in the first solution is about 20 to 40% weight/volume of the first solution and most preferably about 30% weight/volume of the first solution. Dextran can be obtained from several companies including Pharmacia. It is further preferable that the first solution comprises a salt solution. The amount of salt solution in the first solution is preferably about 0.5 M to 1.5 M and more preferably about 0.7 M. Salt solutions that can be used with the present invention include, but are not limited to, sodium chloride, calcium chloride, potassium chloride, magnesium chloride, magnesium sulfate, ammonium chloride and lithium chloride. Preferably, the salt solution comprises calcium chloride. It has been found that the salt solution exerts an aggregating effect on the adsorbent.

The above method provides for separating the adsorbent from the microorganisms and the medium and removing the microorganisms and a portion of the medium from the vessel. Preferably, the adsorbent can be separated from the microorganisms and medium by centrifugation or filtration. Most preferably, the adsorbent is separated from the microorganisms and medium by centrifugation for ten (10) minutes at $\geq$1,000 G to pellet the adsorbent and other particles such as red blood cells.

Step (d) of the above method provides for mixing the microorganisms and a portion of the medium with a second solution in a second vessel to resuspend the microorganisms. After the second solution is added to the vessel, the vessel can be vortexed.

The amount of the second solution that can be added to the vessel in step (d) is dependent upon the milliliters of microorganisms and medium mixed into the second vessel. Generally, about 2 mL of the second solution should be added for every 1 mL of the microorganisms and medium mixed into the second vessel. In a preferred embodiment, 5 mL of microorganisms and medium is mixed into the second vessel with 10 mL of the second solution. Preferably, the second solution comprises a buffered salt solution and/or a saline solution. A preferred saline solution is 0.45% NaCl.

The above method provides for separating the microorganisms from the resulting mixture in step (e). Preferably, this can be done by centrifugation or filtration. Most preferably, this can be done by centrifugation for fifteen (15) minutes at $\geq$3,000 G to pellet the microorganisms.

Also, the microorganisms obtained in step (e) can be resuspended in a buffered salt solution or saline solution again if desired.

A preferred embodiment of the present invention provides for recovering microorganisms from a sample by:
 (a) preparing a sample comprising a medium, an adsorbent, microorganisms and blood or a blood component;
 (b) mixing the sample with a first solution in a first vessel, the first solution comprising dextran and calcium chloride;
 (c) separating the adsorbent and the blood or blood component from the medium and the microorganisms and removing the microorganisms and a portion of the medium from the first vessel;
 (d) mixing the microorganisms and the portion of the medium with a second solution in a second vessel to resuspend the microorganisms; and
 (e) separating the microorganisms from the resulting mixture of step (d).

Step (a) provides for preparing a sample comprising a medium, an adsorbent, microorganisms and blood or a blood component. The type of sample to be tested will determine how the sample will be prepared. Samples that can be used in this method of the present invention can be obtained from any source including, but not limited to, blood, blood products, tissue, ascites, culture media, body fluids, skin, pus, urogenital specimens, feces, foodstuffs, beverages, cosmetic products, pharmaceutical products, healthcare products, surfaces such as floors and tables, and airborne particles such as pollen and dust. The sample may be one that is suspected of having microorganisms or the sample may already have been tested for the presence of microorganisms and have tested positive for microorganisms. The sample may require the addition of a medium and/or the sample may require the addition of an adsorbent. The sample may also require the addition of blood or a blood component. The amount of medium, adsorbent and/or blood or blood component to add to the sample will be dependent upon the estimated number of microorganisms in the sample and could easily be ascertained by one skilled in the art. The amount of adsorbent in the sample should range from about 1-5% weight/volume of the sample.

The adsorbent that is used with this method comprises activated charcoal.

Step (b) provides that the sample and first solution are mixed in a vessel and this can be accomplished by briefly vortexing the vessel. The vessel is a conical tube.

The amount of first solution and sample mixed in step (b) is about 2 mL of the first solution and about 8 mL of the sample.

Preferably, dextran used with this method has a molecular weight of about 70 kD. Also, the amount of dextran in the first solution is about 30% weight/volume of the first solution. The first solution also comprises calcium chloride. The amount of calcium chloride in the first solution is about 0.7 M. It has been found that calcium chloride exerts an aggregating effect on the adsorbent.

The above method provides for separating the adsorbent from the microorganisms and the medium and removing the microorganisms and a portion of the medium from the vessel. The adsorbent is separated from the microorganisms and medium by centrifugation for ten (10) minutes at ≧1,000 G to pellet the adsorbent and other particles such as red blood cells.

Step (d) of the above method provides for mixing the microorganisms and a portion of the medium with a second solution in a second vessel to resuspend the microorganisms. After the second solution is added to the vessel, the vessel can be vortexed. In this embodiment, about 5 mL of microorganisms and medium is mixed into the second vessel with about 10 mL of the second solution. The second solution comprises 0.45% NaCl.

The above method provides for separating the microorganisms from the resulting mixture in step (e). This is done by centrifugation for fifteen (15) minutes at ≧3,000 G to pellet the microorganisms.

The samples used in the methods of the present invention can be obtained from any source including, but not limited to, blood, blood products, tissue, ascites, culture media, body fluids, skin, pus, uro-genital specimens and feces. Samples may also be obtained for detection from foodstuffs and beverages; from cosmetic, pharmaceutical and healthcare products; from surfaces such as floors, tables, and the like; and from airborne particles, such as pollen and dust.

The term "adsorbent" as used in the methods of the present invention is preferably selected from the group provided above, however, for the purposes of this application, the term "adsorbent" includes all adsorbent materials that neutralize, bind, and inhibit antimicrobial substances. These adsorbents include resins as defined in U.S. Pat. No. 4,632,902, and non-resinous adsorbents.

The term "resin" as used herein is a subclass of adsorbents, and is further defined to include naturally occurring and synthetic resins, for example, ion exchange resins, non-functional polymeric resin adsorbents and, in particular, polystyrene resins cross-linked with divinyl benzene.

"Non-resinous adsorbents" as used herein are another subclass of adsorbents and are defined as naturally occurring and synthetic non-resin adsorbents and molecular sieves that can be used for clarifying, deodorizing, decolorizing, and filtering. Some of these non-resinous adsorbents are the same as those used during the production of antibiotics to remove antibiotics from culture medium growing antibiotic-producing bacteria.

These non-resinous adsorbents include various forms of 1) aluminum oxide (alumina), 2) colloidal native hydrated aluminum silicates (clays), such as bentonite, kaolin, and fuller's earth, 3) crystalline hydrated alkali-aluminum silicates (sodium or calcium zeolites), 4) silica (silica gel, silica beads) such as Davisil, 5) siliceous frustules and fragments of various species of diatoms (infusorial earth, diatomaceous earth) such as Celite.™ (Manville Products Corporation, Denver, Colo., USA) and 6) amorphous carbon (in particular, activated carbon) such as Carboraffin, Norit.™ (American Norit Company Inc., Jacksonville, Fla., USA), Opocerbyl and Ultracarbon. Naturally occurring adsorbent activated charcoal, which has been used to prevent the lethal effects of oxidation in transport media and growth media, can also be used. This media has been used for the transport of fastidious organisms such as *Neisseria gonorrhoeae* and the cultivation of *Legionella* species. Non-resinous adsorbents do not require pre-treatment with a surfactant in order to function. Treatment with surfactants may even decrease the adsorbtive capabilities of these materials.

Many of these non-resinous adsorbents remove antimicrobial substances in culture. Preferred non-resinous adsorbents are the colloidal native hydrated aluminum silicates (clay) and the amorphous carbon (activated carbon) groups of adsorbent materials. Additionally preferred materials are fuller's earth or activated charcoal used singularly or in combination.

The samples used in the methods of the present invention contain media or media is added to the sample. Preferably, the media is growth media and the growth media can include general purpose media such as tryptic soy broth, brain heart infusion broth, Columbia broth and Brucella broth.

Suitable surfactants or absorption enhancers may also included in the first and second solutions. Suitable surfactants or absorption enhancers that can be used in the first and/or second solutions include, for example, oleic acid, polyoxyethylene derivatives of fatty acids, partial esters of sorbitol anhydride, such as for example, Tween 20, polyoxyl 40 stearate, polyoxyethylene 50 stearate, fusieates, bile salts, octoxynol and combinations thereof. Suitable surfactants include non-ionic, anionic and cationic surfactants.

EXAMPLES

The present invention is further detailed in the following Examples which are offered by way of illustration and is not intended to limit the invention in any manner. Standard techniques well known in the art or the techniques specifically described below are utilized.

Example 1

Plastic BacT/ALERT FA culture bottles (bioMerieux, Inc.) were inoculated with 10 mL of normal human blood and one of twenty-eight (28) *Staphylococcal* isolates (15 *S. aureus* and 13 *S. e* with 2 mL of a solution (Solution A) designed to promote sedimentation of the charcoal particles. The mixture was then centrifuged for 10 minutes at 1000 G and the supernatant was collected, diluted and centrifuged again at 3,000 G to pellet microorganisms. The pellet was resuspended directly in 0.45% NaCl, adjusted to 0.50-0.63 McFarland and tested in VITEK ID-GPC and AST-GP55 cards.

A more detailed general description of the method is as follows:
1. For each test organism, add 8 mL of positive blood culture to 2 mL of Solution A in a 15 mL conical tube.
2. Mix the contents of the tube and centrifuge the tubes for 10 minutes at 1,000 G to pellet the KBB charcoal and red blood cells.
3. Carefully remove the top 5 mL from each tube containing microorganisms and add to 10 mL of 0.45% NaCl in a 15 mL conical tube.
4. Mix the contents of the tubes and centrifuge for 15 minutes at 3000 G to pellet the bacteria.
5. Remove all of the supernatant and resuspend the pellet in 3 mL of 0.45% NaCl.

Solution A included 30% w/v dextran (70 kD, Pharmacia), 0.15 M NaCl and 0.7 M $CaCl_2$.

This procedure resulted in *Staphylococcal* suspensions macroscopically free of charcoal and red blood cell contamination. However, when tested in VITEK ID-GPC cards, only 43% of isolates were correctly identified (4/15 *S. aureus* and 8/13 *S. epidermidis*). All of the incorrectly identified isolates were designated *Kocuria rosea* or *Kocuria varians*, which is indicative of metabolic inactivity. Further testing of the McFarland suspension with gram stains and cell counts indicate that an insufficient cell density may be the cause of the poor results.

The method described and used in this experiment provides a rapid and inexpensive method for separating adsorbents such as charcoal particles from microorganisms recovered in positive BacT/ALERT FAN bottles or other samples. The method also provides a rapid procedure to separate other particulates such as blood cells.

Example 2

In this Example, three studies are essentially provided. In the first study, several additives were evaluated to find out which enhanced the sedimentation of blood cell samples and colloidal charcoal. In the second study, the synergy of a first solution comprising dextran and calcium chloride was evaluated with respect to the sedimentation of colloidal charcoal and red blood cells. In the third study, several samples containing different microorganisms were tested according to a method of the present invention with various compositions of the first solution.

As stated above, in the first study, several additives were evaluated to find out which enhanced the sedimentation of blood cell samples and colloidal charcoal. In particular, plastic BacT/ALERT FA culture bottles (bioMerieux, Inc.) containing colloidal charcoal and blood cell samples were used to evaluate whether different potential additives enhanced the sedimentation of the blood cell samples and the colloidal charcoal. All of the BacT/ALERT FA culture bottles (bioMerieux, Inc.) tested negative for microorganisms. Eight samples were prepared and for each, 4 mL of a blood cell/colloidal charcoal mixture was removed from one of the BacT/ALERT FA culture bottles and mixed with about 1 mL of one of several different additives. The degree of sedimentation following centrifugation and the additives used are shown in TABLE 1 below. The scale for the degree of sedimentation shown in TABLE 1 is from none to +++ (+++ meaning a high degree of blood cell sedimentation).

TABLE 1

| Sample No. | Composition of Sample | Microorganism(s) Present | Additive | $^a$Degree of Sedimentation |
| --- | --- | --- | --- | --- |
| 1 | Blood/FA broth mixture | None | water | none |
| 2 | Blood/FA broth mixture | None | 3M Calcium Chloride | + |
| 3 | Blood/FA broth mixture | None | 3M Sodium Chloride | +/− |
| 4 | Blood/FA broth mixture | None | 5% Ferric Ammonium Citrate | none |
| 5 | Blood/FA broth mixture | None | 10% 200 kD dextran | ++ |
| 6 | Blood/FA broth mixture | None | 10% 70 kD dextran | + |
| 7 | Blood/FA broth mixture | None | 20% 70 kD dextran | ++ |
| 8 | Blood/FA broth mixture | None | 30% 70 kD dextran | +++ |

$^a$following a 10 minute centrifugation at 160 G

The salts tested caused a marked compaction of the colloidal charcoal particles while the dextran enhanced the sedimentation of blood cells.

In the second study, the synergy of a first solution comprising both dextran and calcium chloride was evaluated with respect to the sedimentation of colloidal charcoal and red blood cells against a first solution comprising dextran and water. Two plastic BacT/ALERT FA culture bottles (bioMerieux, Inc.), one inoculated with *S. aureus* and the other inoculated with *S. epidermidis*, were used in this study. Two 4 mL samples from the bottle containing a blood cell/colloidal charcoal mixture including the microorganism *S. aureus* were removed and two 4 mL samples from the bottle containing a blood cell/colloidal charcoal mixture including the microorganism *S. epidermidis* were removed. A first solution comprising 1 mL of dextran and 0.5 mL of water was added to one of the samples containing *S. aureus* and to one of the samples containing *S. epidermis*. A first solution comprising 1 mL of dextran and 0.5 mL of calcium chloride was added to the other sample containing *S. aureus* and to the other sample containing *S. epidermis*. The degree of sedimentation following centrifugation of each of the samples is shown in TABLE 2 below. The scale for the degree of sedimentation shown in TABLE 2 is from + to ++++ (++++ meaning a high degree of blood cell and colloidal charcoal sedimentation).

TABLE 2

| Sample No. | Composition of Sample | Microorganism Present | Additives | $^a$Degree of Sedimentation |
| --- | --- | --- | --- | --- |
| 1 | Blood/FA broth mixture | *S. aureus* | 1 mL of 30% 70 kD dextran + 0.5 mL water | ++ |
| 2 | Blood/FA broth mixture | *S. aureus* | 1 mL of 30% 70 kD dextran + 0.5 mL 3M CaCl$_2$ | ++++ |
| 3 | Blood/FA broth mixture | *S. epidermidis* | 1 mL of 30% 70 kD dextran + 0.5 mL water | + |
| 4 | Blood/FA broth mixture | *S. epidermidis* | 1 mL of 30% 70 kD dextran + 0.5 mL 3M CaCl$_2$ | ++++ |

$^a$following a 10 minute centrifugation at 160 G

As can be seen in TABLE 2, the combination of dextran and calcium chloride sedimented the colloidal charcoal and blood cells in the sample to a higher degree than the combination of dextran and water.

In the third part of this study, several samples containing different microorganisms were tested according to a method of the present invention with various compositions of the first solution. In particular, plastic BacT/ALERT FA culture bottles, which contain colloidal charcoal in a medium, were inoculated with sample and isolates as follows: (1) BacT/ALERT FA culture bottles were inoculated with 10 mL of normal human blood and the isolate *S. aureus* (Group 1); (2) BacT/ALERT FA culture bottles were inoculated with 10 mL of normal human blood and the isolate *P. aeruginosa* (Group 2); (3) BacT/ALERT FA culture bottles were inoculated with 10 mL of normal human blood and the isolate *E. coli* (Group 3); (4) BacT/ALERT FA culture bottles were inoculated with 10 mL of normal human blood and the isolate *E. faecalis*

(Group 4); (5) BacT/ALERT FA culture bottles were inoculated with 10 mL of normal human blood and the isolate *S. pyogenes* (Group 5); (6) BacT/ALERT FA culture bottles were inoculated with 10 mL of normal human blood and the isolate *S. epidermis* (Group 6); (7) BacT/ALERT FA culture bottles were inoculated with 10 mL of normal human blood and the isolate *N. meningitidis* (Group 7); and (8) BacT/ALERT FA culture bottles were inoculated with 10 mL of normal human blood and the isolate *S. maltophilia* (Group 8). 4 mL samples recovered from the bottles were then mixed with one of the following four first solutions:

Solution A=1 mL 30% dextran and 0.25 mL 3M $CaCl_2$ (140 mM final)

Solution B=1.5 mL physiological saline

Solution C=1 mL 30% dextran and 0.5 mL 3M $CaCl_2$ (280 mM final)

Solution D=1 mL 30% dextran and 0.25 mL 3M CaCl2 (140 mM final)

Each the mixtures was then centrifuged for 10 minutes and the supernatant was collected, diluted and centrifuged again to pellet microorganisms. The mixtures including Solution A were rentrifuged at 1,000 rpm. The mixtures including Solution B or Solution C were centrifuged at 1,200 rpm. The mixtures including Solution D were centrifuged at 3,000 rpm. The pellets were each resuspended directly in 0.45% NaCl. Each microbial suspension was assessed for purity by gram staining a smear of the suspension. The results are shown below in TABLE 3.

and blood cells from a variety of microorganisms. The bacterial suspensions recovered by this procedure were sufficiently pure to be suitable for rapid identification techniques such as the VITEK 2 card reagents. Separation of colloidal charcoal particles and microorganisms were poor in the absence of the calcium salt, i.e., samples mixed with Solution B.

Thus, while there have been described what are presently believed to be the preferred embodiments of the present invention, those skilled in the art will realize that other and further embodiments can be made without department from the spirit and scope of the invention, and it is intended to include all such further modifications and changes as come within the true scope of the invention.

What is claimed is:

1. A method for recovering microorganisms selected from the group consisting of bacteria and yeast from a sample, comprising the steps of:
    (a) mixing a sample comprising a medium, an adsorbent and microorganisms with a first solution comprising dextran and calcium chloride in a first vessel;
    (b) separating said adsorbent from said medium and said microorganisms and removing said microorganisms and a portion of said medium from said first vessel;
    (c) mixing said microorganisms and said portion of said medium with a second solution in a second vessel to resuspend said microorganisms; and

TABLE 3

| | | | | Gram Stain Results | | |
|---|---|---|---|---|---|---|
| Group | Microorganism in Sample | Solution | Centrifuged at (rpm) | Degree of Charcoal Contamination | Bacterial Density | Degree of Red Blood Cell Contamination |
| 1 | *S. aureus* | A | 1,000 | 2+ | 3+ | 1+ |
| | *S. aureus* | B | 1,200 | 4+ | +/− | 1+ |
| | *S. aureus* | C | 1,200 | 1+ | 3+ | +/−−1+ |
| | *S. aureus* | D | 3,000 | 1-2+ | 2+ | +/− |
| 2 | *P. aeruginosa* | A | 1,000 | 1+ | 3+ | 1+ |
| | *P. aeruginosa* | B | 1,200 | 4+ | 3+ | 1+ |
| | *P. aeruginosa* | C | 1,200 | 1+ | 3+ | 1+ |
| | *P. aeruginosa* | D | 3,000 | +/− | 4+ | +/− |
| 3 | *E. coli* | A | 1,000 | 3+ | 3+ | 1+ |
| | *E. coli* | B | 1,200 | 3+ | 3+ | 1+ |
| | *E. coli* | C | 1,200 | 2+ | 3+ | 1+ |
| | *E. coli* | D | 3,000 | 1+ | 3+ | +/− |
| 4 | *E. faecalis* | A | 1,000 | 3+ | 4+ | 1+ |
| | *E. faecalis* | B | 1,200 | 2+ | 3+ | 1+ |
| | *E. faecalis* | C | 1,200 | 1+ | 3+ | 1+ |
| | *E. faecalis* | D | 3,000 | +/− | 4+ | +/− |
| 5 | *S. pyogenes* | A | 1,000 | 2+ | 2+ | 1+ |
| | *S. pyogenes* | B | 1,200 | 1+ | 1+ | 1+ |
| | *S. pyogenes* | C | 1,200 | nil | nil | nil |
| | *S. pyogenes* | D | 3,000 | +/− | 3+ | 1+ |
| 6 | *S. epidermidis* | A | 1,000 | 1+ | 3+ | +/− |
| | *S. epidermidis* | B | 1,200 | 4+ | 1+ | 1+ |
| | *S. epidermidis* | C | 1,200 | 1+ | 3+ | +/− |
| | *S. epidermidis* | D | 3,000 | 1+ | 2+ | 1+ |
| 7 | *N. meningitidis* | A | 1,000 | NT | NT | NT |
| | *N. meningitidis* | B | 1,200 | 4+ | 3+ | +/− |
| | *N. meningitidis* | C | 1,200 | 1+ | 2+ | +/− |
| | *N. meningitidis* | D | 3,000 | 1+ | 2+ | +/− |
| 8 | *S. maltophilia* | A | 1,000 | NT | NT | NT |
| | *S. maltophilia* | B | 1,200 | 4+ | 3+ | +/− |
| | *S. maltophilia* | C | 1,200 | 1+ | 2+ | +/− |
| | *S. maltophilia* | D | 3,000 | +/− | 3+ | +− |

Solution D was found to provide the most optimal conditions for separation, by sedimentation, of charcoal particles (d) separating said microorganisms from the resulting mixture of step (c).

2. The method according to claim 1, wherein said adsorbent is selected from the group consisting on aluminum oxide, colloidal native hydrated aluminum silicates, crystalline hydrated alkali-aluminum silicates, silica, siliceous frustules, fragments of various species of diatoms, amorphous carbon, ion exchange resins, non-functional polymeric resin absorbents, polystyrene resin cross-linked with divinyl benzene, charcoal particles, activated charcoal, charcoal bound to fibers, fuller's earth bound to fibers, charcoal bound to fuller's earth and combinations thereof.

3. The method according to clam 1, wherein said first solution and said sample are mixed in step (a) at a ratio of about one to four.

4. The method according to claim 3, wherein about 2 mL of said first solution is mixed with about 8 mL of said sample in step (a).

5. The method according to claim 1, wherein said second solution comprises a buffered salt solution and/or a saline solution.

6. The method according to claim 1, wherein said sample further comprises blood or a blood component and said blood or blood component is separated along with said adsorbent from said medium and said microorganisms in step (b).

7. The method according to claim 1, wherein said sample further comprises plasma or serum and said plasma or serum is separated along with said medium and said microorganisms from said adsorbent in step (b) and separated from said microorganisms in step (d).

8. A method for recovering microorganisms selected from the group consisting of bacteria and yeast from a sample, comprising the steps of:
  (a) preparing a sample comprising a medium, an adsorbent and microorganisms;
  (b) mixing said sample with a first solution comprising dextran and calcium chloride in a first vessel;
  (c) separating said adsorbent from said medium and said microorganisms and removing said microorganisms and a portion of said medium from said first vessel;
  (d) mixing said microorganisms and said portion of said medium with a second solution in a second vessel to resuspend said microorganisms; and
  (e) separating said microorganisms from the resulting mixture of step (d).

9. The method according to claim 8, wherein said sample further comprises blood or a blood component and said blood or blood component is separated along with said adsorbent from said medium and said microorganisms in step (c).

10. The method according to claim 8, wherein said sample further comprises plasma or serum and said plasma or serum is separated along with said medium and said microorganisms from said adsorbent in step (c) and separated from said microorganisms in step (e).

11. The method according to claim 8, wherein said first solution and said sample are mixed in step (b) at a ratio of about one to four.

12. A method for recovering bacteria or yeast from a culture media comprising a sample, comprising the steps of:
  (a) combining said culture media comprising a sample comprising blood or a blood component with an adsorbent comprising charcoal particles to form a mixture;
  (b) combining said mixture with a first solution in a first vessel, said first solution comprising dextran and calcium chloride;
  (c) separating said adsorbent a and said blood or blood component from said media and said bacteria or yeast and removing said bacteria or yeast and a portion of said media from said first vessel;
  (d) mixing said bacteria or yeast and said portion of said media with a second solution in a second vessel to resuspend said bacteria or yeast; and
  (e) separating said bacteria or yeast from the resulting mixture of step (d).

13. The method of claim 1, wherein said dextran has a molecular weight of about 40 to about 210 kD.

14. The method of claim 8, wherein said dextran has a molecular weight of about 40 to about 210 kD.

15. The method of claim 1, wherein the amount of dextran in said first solution is about 20% to about 40% weight/volume.

16. The method of claim 8, wherein the amount of dextran in said first solution is about 20% to about 40% weight/volume.

17. The method of claim 1, wherein the amount of calcium chloride in said first solution is about 0.5 M to about 1.5 M.

18. The method of claim 8, wherein the amount of calcium chloride in said first solution is about 0.5 M to about 1.5 M.

* * * * *